US00PP30785P2

(12) United States Plant Patent
Barnes

(10) Patent No.: US PP30,785 P2
(45) Date of Patent: Aug. 6, 2019

(54) ***CALIBRACHOA* PLANT NAMED 'BBCAL82201'**

(50) Latin Name: ***Calibrachoa* sp.**
Varietal Denomination: BBCAL82201

(71) Applicant: Brent D. Barnes, Riverside, CA (US)

(72) Inventor: Brent D. Barnes, Riverside, CA (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/998,101

(22) Filed: Jun. 28, 2018

(51) Int. Cl.
*A01H 5/02* (2018.01)

(52) U.S. Cl.
USPC ..... Plt./413

(58) Field of Classification Search
USPC ..... Plt./413
See application file for complete search history.

*Primary Examiner* — Annette H Para
(74) *Attorney, Agent, or Firm* — C. A. Whealy

(57) ABSTRACT

A new and distinct *Calibrachoa* plant named 'BBCAL82201', characterized by its compact, upright to outwardly spreading and mounding to trailing plant habit; moderately vigorous to vigorous growth habit; freely branching habit; dense and bushy appearance; early and freely flowering habit; orange red-colored petals with dark greyed purple-colored centers; and good garden performance.

1 Drawing Sheet

Botanical designation: *Calibrachoa* sp.
Cultivar denomination: 'BBCAL82201'.

BACKGROUND OF THE INVENTION

The present invention relates to a new and distinct cultivar of *Calibrachoa* plant, botanically known as *Calibrachoa* sp. and hereinafter referred to by the name 'BBCAL82201'.

The new *Calibrachoa* plant is a product of a planned breeding program conducted by the Inventor in Bonsall, Calif. The objective of the breeding program is to create new uniform and freely-branching *Calibrachoa* plants with unique and attractive flower colors and patterns and good garden performance.

The new *Calibrachoa* plant originated from a cross-pollination conducted by the Inventor in Bonsall, Calif. on Aug. 26, 2015 of *Calibrachoa* sp. 'Duecahulgo', disclosed in U.S. Plant Pat. No. 27,652, as the female, or seed, parent with a proprietary seedling selection of *Calibrachoa* sp. identified as code number 14CG043-02, not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on May 17, 2016.

Asexual reproduction of the new *Calibrachoa* plant by vegetative terminal cuttings in a controlled greenhouse environment in Bonsall, Calif. since May 17, 2016 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBCAL82201'. These characteristics in combination distinguish 'BBCAL82201' as a new and distinct *Calibrachoa* plant:

1. Compact, upright to outwardly spreading and mounding to trailing plant habit.
2. Moderately vigorous to vigorous growth habit.
3. Freely branching habit; dense and bushy appearance.
4. Early and freely flowering habit.
5. Orange red-colored petals with dark greyed purple-colored centers.
6. Good garden performance.

Plants of the new *Calibrachoa* differ primarily from plants of the female parent, 'Duecahulgo', in the following characteristics:

1. Plants of the new *Calibrachoa* are more freely branching than plants of 'Duecahulgo'.
2. Plants of the new *Calibrachoa* and 'Duecahulgo' differ in flower color as flowers of plants of 'Duecahulgo' are orange in color with brownish red-colored centers.
3. Plants of the new *Calibrachoa* have good garden performance and are more tolerant to pathogens common to *Calibrachoa* plants than plants of 'Duecahulgo'.

Plants of the new *Calibrachoa* differ primarily from plants of the male parent selection in the following characteristics:

1. Plants of the new *Calibrachoa* are more outwardly spreading than and not as upright as plants of the male parent selection.
2. Plants of the new *Calibrachoa* are more freely branching than plants of the male parent selection.

3. Plants of the new *Calibrachoa* and the male parent selection differ in flower color as flowers of plants of the male parent selection are orange in color with red-colored centers.
4. Plants of the new *Calibrachoa* have good garden performance and are more tolerant to pathogens common to *Calibrachoa* plants than plants of the male parent selection.

Plants of the new *Calibrachoa* can be compared to plants of the *Calibrachoa* sp. 'USCALI11', disclosed in U.S. Plant Pat. No. 14,968. In side-by-side comparisons, plants of the new *Calibrachoa* differ primarily from plants of 'USCALI11' in the following characteristics:

1. Plants of the new *Calibrachoa* are more outwardly spreading than and not as upright as plants of 'USCALI11'.
2. Plants of the new *Calibrachoa* and 'USCALI11' differ in flower color as flowers of plants of 'USCALI11' are light red purple in color.

Plants of the new *Calibrachoa* can also be compared to plants of the *Calibrachoa* sp. 'USCALI51', disclosed in U.S. Plant Pat. No. 14,874. In side-by-side comparisons, plants of the new *Calibrachoa* differ primarily from plants of 'USCALI51' in the following characteristics:

1. Plants of the new *Calibrachoa* are more outwardly spreading than and not as upright as plants of 'USCALI51'.
2. Plants of the new *Calibrachoa* and 'USCALI51' differ in flower color as flowers of plants of 'USCALI51' are violet in color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'BBCAL82201' grown in a container.

The photograph at the top of the sheet is a close-up view of a typical flowering plant of 'BBCAL82201'.

DETAILED BOTANICAL DESCRIPTION

The aforementioned photographs and following observations and measurements describe plants grown during the spring in 10-cm containers in an acrylic-covered greenhouse in Carleton, Mich. and under cultural practices typical of commercial *Calibrachoa* production. During the production of the plants, day and night temperatures ranged from 18° C. to 24° C. Plants were twelve weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'BBCAL82201'.

Parentage:

*Female, or seed, parent.*—*Calibrachoa* sp. 'Duecahulgo', disclosed in U.S. Plant Pat. No. 27,652.

*Male, or pollen, parent.*—Proprietary seedling selection of *Calibrachoa* sp. identified as code number 14CG043-02, not patented.

Propagation:

*Type.*—By vegetative terminal cuttings.

*Time to initiate roots, summer.*—About five to seven days at ambient temperatures ranging from 17° C. to 29° C.

*Time to initiate roots, winter.*—About seven to ten days at ambient temperatures ranging from 17° C. to 21° C.

*Time to produce a rooted plant, summer.*—About four to five weeks at ambient temperatures ranging from 17° C. to 29° C.

*Time to produce a rooted plant, winter.*—About five to six weeks at ambient temperatures ranging from 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading and mounding to trailing plant habit; moderately vigorous to vigorous growth habit; moderate growth rate; freely branching habit with about four primary lateral branches each with about five to six secondary branches; dense and bushy appearance.

*Plant height, soil level to top of foliar plane.*—About 12.5 cm.

*Plant height, soil level to top of floral plane.*—About 14 cm.

*Plant diameter.*—About 28 cm by 31 cm.

Lateral branch description:

*Length.*—About 20 cm.

*Diameter.*—About 2 mm.

*Internode length.*—About 1.6 cm.

*Strength.*—Strong.

*Aspect.*—About 45° to 85° from stem axis.

*Texture and luster.*—Minute pubescence; matte.

*Color, developing.*—Close to 146D.

*Color, developed.*—Close to 146C.

Leaf description:

*Arrangement.*—Before flowering, alternate; after flowering, opposite; leaves simple.

*Length.*—About 3 cm.

*Width.*—About 1.3 cm.

*Shape.*—Elliptical.

*Apex.*—Rounded.

*Base.*—Attenuate.

*Margin.*—Entire.

*Texture and luster, upper and lower surfaces.*—Minute pubescence; matte.

*Venation pattern.*—Pinnate; arcuate.

*Color.*—Developing leaves, upper surface: Close to 146A. Developing leaves, lower surface: Close to 147B. Fully expanded leaves, upper surface: Close to 147A; venation, close to 147B. Fully expanded leaves, lower surface: Close to 147B; venation, close to 147C.

*Petioles.*—Length: About 5 mm. Diameter: About 2 mm. Strength: Moderately strong. Texture and luster, upper and lower surfaces: Minute pubescence; matte. Color, upper and lower surfaces: Close to 146C.

Flower description:

*Flower type and flowering habit*.—Single salverform flowers arising from leaf axils; freely flowering habit with typically about 191 flowers and flower buds developing per plant; flowers face upright, outwardly to nodding.

*Fragrance*.—None detected.

*Natural flowering season*.—Plants of the new *Calibrachoa* begin flowering about six weeks after planting; plants flower continuously from the spring though the summer until frost.

*Flower longevity*.—Individual flowers last about four to five days on the plant; flowers persistent.

*Flower buds*.—Length: About 2.5 cm. Diameter: About 7 mm. Shape: Oblong, elongate. Texture and luster: Minute pubescence; matte. Color: Close to 166D.

*Flower diameter*.—About 3.5 cm by 4 cm.

*Flower length* (*height*).—About 2.4 cm.

*Flower throat diameter*.—About 5 mm by 10 mm.

*Flower tube length*.—About 2 cm.

*Flower tube diameter*.—About 5 mm.

*Corolla*.—Arrangement: Five fused petals opening into a flared trumpet. Petal lobe length (from throat): About 1.7 cm. Petal lobe width: About 2 cm. Petal shape: Fan-shaped, somewhat cordate. Petal apex: Emarginate; recurving with development. Petal margin: Entire; slightly undulate. Petal texture and luster, upper surface: Smooth, glabrous, velvety; matte. Petal texture and luster, lower surface: Smooth, glabrous; matte. Throat texture and luster: Smooth, glabrous; glossy. Tube texture and luster: Minute pubescence; matte. Color: Petal lobe, when opening, upper surface: Close to 181A to 181B. Petal lobe, when opening, lower surface: Close to 177D. Petal lobe, fully opened, upper surface: Towards the margins, close to 34A to 34B; center, close to 187A; venation, close to 183B; color becoming closer to 179B to 179C with development. Petal lobe, fully opened, lower surface: Close to 181C to 181D; venation, close to 183A and 183B; color becoming closer to 182D with development. Throat: Close to 163B; venation, close to 177B. Tube: Close to 152D; venation, close to 187B.

*Calyx*.—Arrangement: One star-shaped calyx tube with five sepals fused towards the base and arranged in a single whorl. Length: About 1.6 cm. Diameter: About 1.7 cm. Sepal length: About 1.1 cm. Sepal width: About 3 mm. Sepal shape: Lanceolate to narrowly ligulate. Sepal apex: Acute. Sepal margin: Entire. Sepal texture and luster, upper and lower surfaces: Minute pubescence; matte. Sepal color, when developing, upper and lower surfaces: Close to 146A. Sepal color, developed, upper and lower surfaces: Close to 146A.

*Peduncles*.—Length: About 7 mm. Diameter: About 1 mm. Angle: About 45° to 55° from stem axis. Strength: Strong. Texture and luster: Minute pubescence; matte. Color: Close to 146B.

*Reproductive organs*.—Stamens: Quantity: Five per flower. Filament length: About 8 mm. Filament color: Close to 145D. Anther size: About 1 mm by 1 mm. Anther shape: Round. Anther color: Close to 6A. Pollen amount: Scarce. Pollen color: Close to 13B. Pistils: Quantity: One per flower. Pistil length: About 1.2 cm. Style length: About 6 mm. Style color: Close to 146C. Stigma diameter: About 1 mm. Stigma shape: Round. Stigma color: Close to 146B. Ovary color: Close to 145A. Seeds and fruits: To date, seed and fruit development have not been observed on plants of the new *Calibrachoa*.

Garden performance: Plants of the new *Calibrachoa* have been observed to have good garden performance and tolerate wind, rain and to be suitable for USDA Hardiness Zones 9a to 11b.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'BBCAL82201' as illustrated and described.

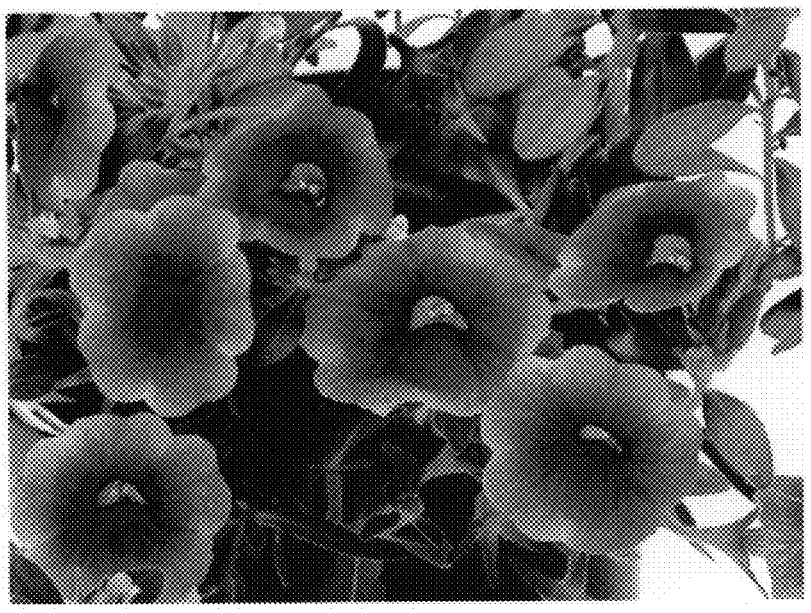
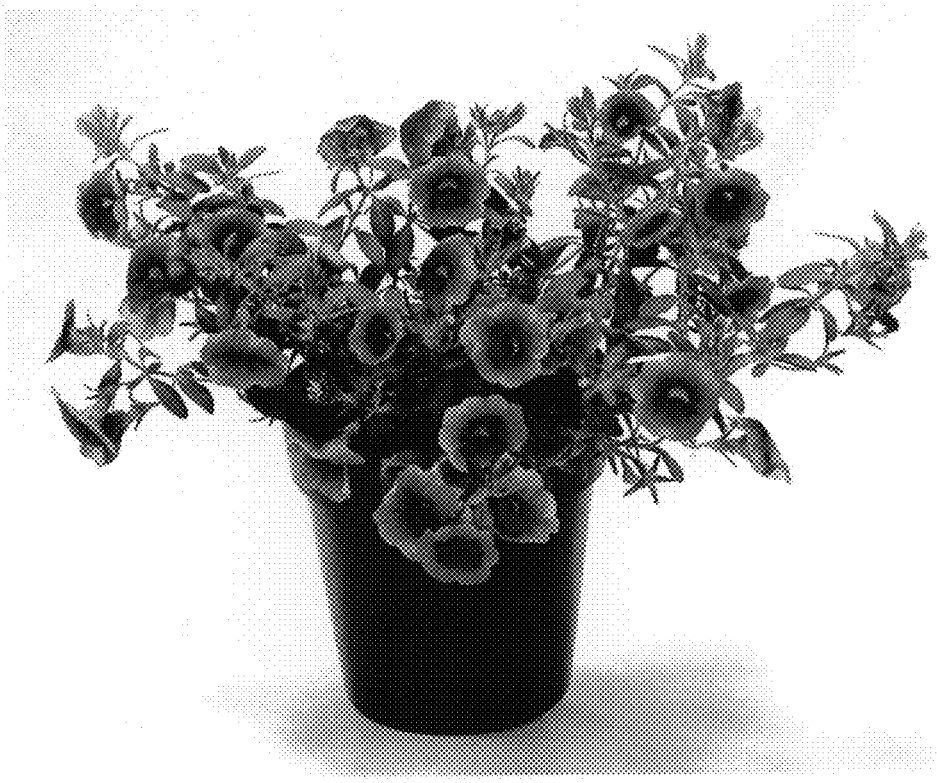

* * * * *